United States Patent
Graves et al.

(10) Patent No.: US 10,624,707 B2
(45) Date of Patent: Apr. 21, 2020

(54) ROBOTIC SURGICAL SYSTEM AND METHOD FOR COMMUNICATING SYNCHRONOUS AND ASYNCHRONOUS INFORMATION TO AND FROM NODES OF A ROBOTIC ARM

(71) Applicant: Verb Surgical Inc., Mountain View, CA (US)

(72) Inventors: Philip L. Graves, San Jose, CA (US); Klaus R. Zietlow, Piedmont, CA (US)

(73) Assignee: Verb Surgical Inc., Mountain View, CA (US)

( * ) Notice: Subject to any disclaimer, the term of this patent is extended or adjusted under 35 U.S.C. 154(b) by 142 days.

(21) Appl. No.: 15/707,503

(22) Filed: Sep. 18, 2017

(65) Prior Publication Data

US 2019/0083190 A1 Mar. 21, 2019

(51) Int. Cl.
| | |
|---|---|
| A61B 34/00 | (2016.01) |
| A61B 34/37 | (2016.01) |
| H04L 1/00 | (2006.01) |
| H04L 1/16 | (2006.01) |
| H04L 12/801 | (2013.01) |

(52) U.S. Cl.
CPC .............. *A61B 34/70* (2016.02); *A61B 34/37* (2016.02); *H04L 1/0083* (2013.01); *H04L 1/1664* (2013.01); *H04L 1/1671* (2013.01); *H04L 47/10* (2013.01); *H04L 2001/0095* (2013.01)

(58) Field of Classification Search
None
See application file for complete search history.

(56) References Cited

U.S. PATENT DOCUMENTS

| | | | |
|---|---|---|---|
| 7,757,028 B2 | 7/2010 | Druke et al. | |
| 8,072,999 B1 * | 12/2011 | Cline | H04L 12/437 |
| | | | 370/431 |
| 9,544,258 B2 | 1/2017 | Bunte et al. | |
| 2006/0074525 A1 | 4/2006 | Close et al. | |
| 2007/0112463 A1 | 5/2007 | Roh et al. | |
| 2007/0150631 A1 * | 6/2007 | Druke | B25J 9/1661 |
| | | | 710/244 |
| 2008/0144526 A1 | 6/2008 | Hall et al. | |
| 2010/0145521 A1 | 6/2010 | Prisco et al. | |
| 2010/0234857 A1 * | 9/2010 | Itkowitz | G09B 23/285 |
| | | | 606/130 |
| 2011/0112696 A1 | 5/2011 | Yodfat et al. | |
| 2012/0039162 A1 | 2/2012 | Druke et al. | |
| 2013/0245375 A1 | 9/2013 | Dimaio et al. | |
| 2013/0345875 A1 | 12/2013 | Brooks et al. | |

(Continued)

OTHER PUBLICATIONS

International Search Report and Written Opinion for PCT Application No. PCT/US2018/042930, dated Oct. 1, 2018, pp. 1-9.

(Continued)

*Primary Examiner* — Jason E Mattis
*Assistant Examiner* — Hong Shao
(74) *Attorney, Agent, or Firm* — Brinks Gilson & Lione

(57) ABSTRACT

A robotic surgical system is disclosed having a ring network for communicating information between a controller and nodes of one or more robotic arms. A communications protocol is described by which synchronous and asynchronous information can be communicated to and from the nodes of the robotic arms. Also disclosed are various aspects of a physical layer that can be used with the network.

20 Claims, 15 Drawing Sheets

(56) References Cited

U.S. PATENT DOCUMENTS

| | | |
|---|---|---|
| 2014/0210520 A1 | 7/2014 | Harris |
| 2015/0078746 A1 | 3/2015 | Spock et al. |
| 2016/0338676 A1 | 11/2016 | Berger et al. |
| 2017/0097631 A1 | 4/2017 | Linnell et al. |
| 2018/0303482 A1 | 10/2018 | Shelton et al. |
| 2019/0083186 A1 | 3/2019 | Zietlow et al. |
| 2019/0083190 A1 | 3/2019 | Graves et al. |

OTHER PUBLICATIONS

International Search Report and Written Opinion for PCT Application No. PCT/US2018/042922, dated Oct. 1, 2018, pp. 1-10.
International Search Report and Written Opinion in International Application No. PCT/US2019/026582, dated Jul. 9, 2019, 11 pages.
Non-Final Office Action, and Form 892 Notice of References, in U.S. Appl. No. 15/707,449, dated Dec. 20, 2019, 15 pages.

* cited by examiner

| Packet Framing Constant (0x4210) | Sequence | | |
| --- | --- | --- | --- |
| | Channel Id | Data Payload (13 words) | CRC16 |
| | Error / Sync | | |
| Payload Data Type | | | |

FIG. 5

ROBOTIC SURGICAL SYSTEM AND METHOD FOR COMMUNICATING SYNCHRONOUS AND ASYNCHRONOUS INFORMATION TO AND FROM NODES OF A ROBOTIC ARM

BACKGROUND

Robotic surgical systems allow healthcare practitioners to achieve greater accuracy, automation, and/or less-invasive approaches while performing a variety of diagnostic and/or therapeutic procedures. Such technologies are broadly applicable to a variety of medical specialties, ranging from ophthalmology and anesthesiology, to orthopedics and interventional radiology. Some robotic surgical systems incorporate sophisticated robotics and visualization technology for performing minimally-invasive surgeries that can lead to reduced scarring and shorter recover times. One example of a minimally-invasive surgery is a laparoscopic procedure, which typically involves creating a number of small incisions in the patient (e.g., in the abdomen), and introducing one or more tools and at least one camera through the incisions into the patient. The surgical procedure is then performed using the introduced tools, with the visualization aid provided by a camera. At least one of the introduced instruments may be attached to one or more robotic anus operated remoted by a user (e.g., a surgeon).

BRIEF DESCRIPTION OF THE DRAWINGS

FIGS. 4 and 5 are illustrations of a multi-node message of an embodiment.

DETAILED DESCRIPTION

Introduction

The following embodiments describe a robotic surgical system having a ring network for communicating information between a controller and nodes of one or more robotic arms. A communications protocol is described by which synchronous and asynchronous information can be communicated to and from the nodes of the robotic arms. Also disclosed are various aspects of a physical layer that can be used with the network. Before turning to embodiments, the following sections provide examples of a robotic surgical system and a robotic arm.

Example of a Robotic Surgical System

Figure 1:
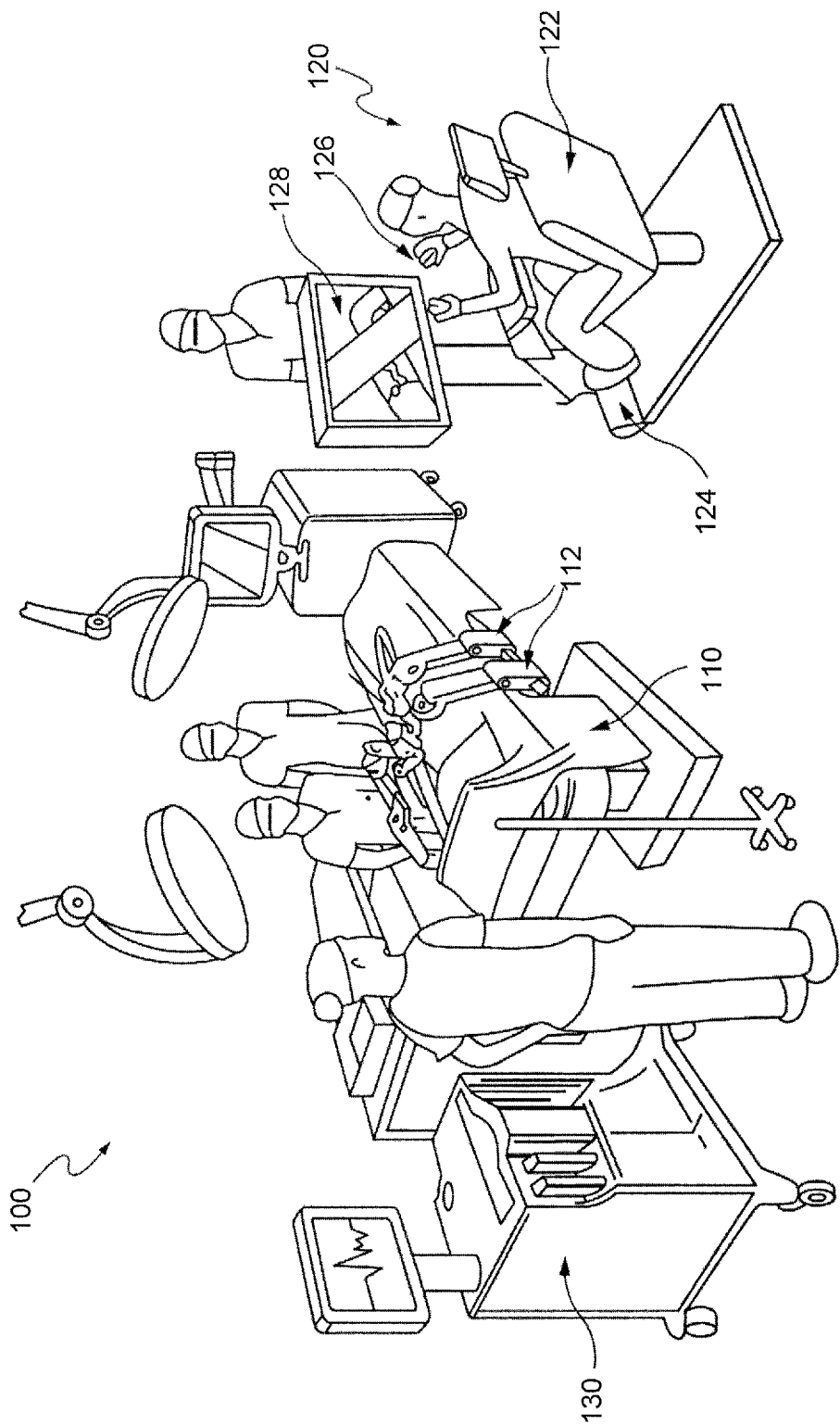
FIG. 1 is an illustration of an operating room arrangement of a robotic surgical system of an embodiment.

Turning now to the drawings, FIG. 1 is a diagram illustrating an example operating room environment with a surgical robotic system 100, in accordance with aspects of the subject technology. It should be noted that this is merely an example for illustration purposes and other arrangements and components can be used. Accordingly, none of the details presented herein should be read into the claims unless explicitly recited therein.

As shown in FIG. 1, the surgical robotic system 100 comprises a surgeon console 120, a control tower 130, and one or more surgical robotic arms 112 located at a surgical robotic platform 110 (e.g., a table or a bed etc.), where surgical tools with end effectors are attached to the distal ends of the robotic arms 112 for executing a surgical procedure. The robotic arms 112 are shown as a table-mounted system, but in other configurations, the robotic arms may be mounted in a cart, ceiling or sidewall, or other suitable support surface.

Generally, a user, such as a surgeon or other operator, may use the user console 120 to remotely manipulate the robotic arms 112 and/or surgical instruments (e.g., tele-operation). The user console 120 may be located in the same operating room as the robotic system 100, as shown in FIG. 1. In other environments, the user console 120 may be located in an adjacent or nearby room, or tele-operated from a remote location in a different building, city, or country. The user console 120 may comprise a seat 122, foot-operated controls 124, one or more handheld user interface devices 126, and at least one user display 128 configured to display, for example, a view of the surgical site inside a patient. As shown in the exemplary user console 120, a surgeon located in the seat 122 and viewing the user display 128 may manipulate the foot-operated controls 124 and/or handheld user interface devices 126 to remotely control the robotic arms 112 and/or surgical instruments mounted to the distal ends of the arms.

In some variations, a user may also operate the surgical robotic system 100 in an "over the bed" (OTB) mode, in which the user is at the patient's side and simultaneously manipulates a robotically-driven tool/end effector attached thereto (e.g., with a handheld user interface device 126 held in one hand) and a manual laparoscopic tool. For example, the user's left hand may be manipulating a handheld user interface device 126 to control a robotic surgical component, while the user's right hand may be manipulating a manual laparoscopic tool. Thus, in these variations, the user may perform both robotic-assisted minimally-invasive surgery (MIS) and manual laparoscopic surgery on a patient.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 120 may utilize the foot-operated controls 124 and/or user interface devices 126 to manipulate various end effectors and/or imaging systems to perform the surgery. Manual assistance may also be provided at the procedure table by sterile-gowned personnel, who may perform tasks including but not limited to, retracting tissues or performing manual repositioning or tool exchange involving one or more robotic arms 112. Nonsterile personnel may also be present to assist the surgeon at the user console 120. When the procedure or surgery is completed, the robotic system 100 and/or user console 120 may be configured or set in a state to facilitate one or more post-operative procedures, including but not limited to, robotic system 100 cleaning and/or sterilization, and/or healthcare record entry or printout, whether electronic or hard copy, such as via the user console 120.

In some aspects, the communication between the robotic platform 110 and the user console 120 may be through the control tower 130, which may translate user commands from the user console 120 to robotic control commands and transmit to the robotic platform 110. The control tower 130 may also transmit status and feedback from the robotic platform 110 back to the user console 120. The connections between the robotic platform 110, the user console 120, and the control tower 130 may be via wired and/or wireless connections, and may be proprietary and/or performed using any of a variety of data communication protocols. Any wired connections may be optionally built into the floor and/or walls or ceiling of the operating room. The surgical robotic system 100 may provide video output to one or more displays, including displays within the operating room as well as remote displays accessible via the Internet or other networks. The video output or feed may also be encrypted to ensure privacy and all or portions of the video output may be saved to a server or electronic healthcare record system.

Figure 2:
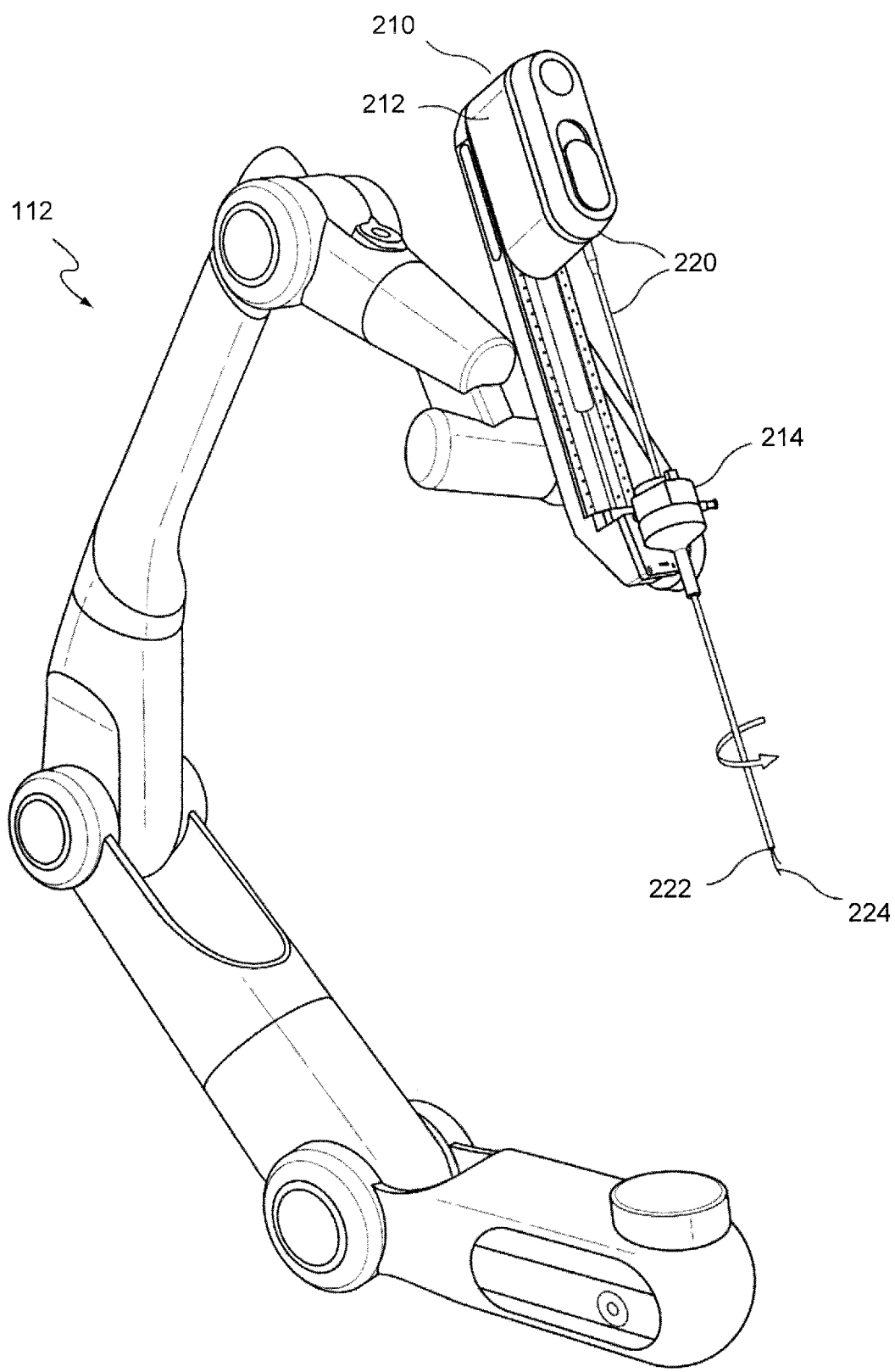
FIG. 2 is an illustration of a robotic arm of an embodiment.

FIG. 2 is a diagram illustrating one exemplary design of a robotic arm, tool drive, and cannula loaded with a surgical tool, in accordance with aspects of the subject technology. As shown in FIG. 2, the example surgical robotic arm 112 may include a plurality of links and a plurality of actuated joint modules for actuating the plurality of links relative to one another. The joint modules may include various types, such as a pitch joint or a roll joint, which may substantially constrain the movement of the adjacent links around certain axes relative to others. Also shown in the exemplary design of FIG. 2, a tool drive 210 may be attached to the distal end of the robotic arm 112. The tool drive 210 may include a base or stage 212 and a cannula 214 coupled to the end of the tool drive 210 to receive and guide a surgical instrument 220 (e.g., endoscopes, staplers, etc.). The surgical instrument (or tool) 220 may include a robotic wrist 222 and one or more end effectors 224 at the distal end of the tool. The plurality of the joint modules of the robotic arm 112 can be actuated to position and orient the tool drive 210, which actuates the robotic wrist 222 and the one or more end effectors 224 for robotic surgeries.

The robotic arm 112 also includes a plurality of nodes between adjacent links. As used herein, a "node" can generally refer to a component that communicates with a controller of the robotic surgical system. A "node," which will sometimes be referred to herein as a "joint module," can be used for actuating one link of the robotic arm with respect to another (e.g., by using a motor to move a series of pulleys and a series of bands connecting the pulleys to facilitate four-bar linkage movement). In response to commands from an external controller (discussed in more detail below), the nodes can be used to articulate the various links in the robotic arm to manipulate the arm for a surgical procedure.

Examples of nodes include, but are not limited to, one or more of the following: a single motor (e.g., a servomotor, a pivot-link motor, a joint motor, and a tool drive motor), a dual motor (e.g., with a differential gear drive to combine the individual motor outputs), a wireless tool interface (e.g., a tool wireless board), a force/torque sensor (e.g., an encoder that detects and provides signals characterizing at least one of force and torque multi-directionality applied to the robotic arm between the arm links/segments), an input/output board, a component that monitors power and/or communication links, or any other component that can receive/transmit data. A node can also include various electronics, such as, but not limited to, a motor controller/driver, signal processors, and/or communications electronics on a circuit board. As will be discussed in more detail below, the nodes can be arranged in a ring network for communicating with an external controller. In one embodiment, the control of the tool of the robotic arm is done via a wireless tool interface, so as to provide electrical isolation between the tool and the other components of the robot for safety reasons.

Example of a Communication Network of a Robotic Surgical System

Figure 3:
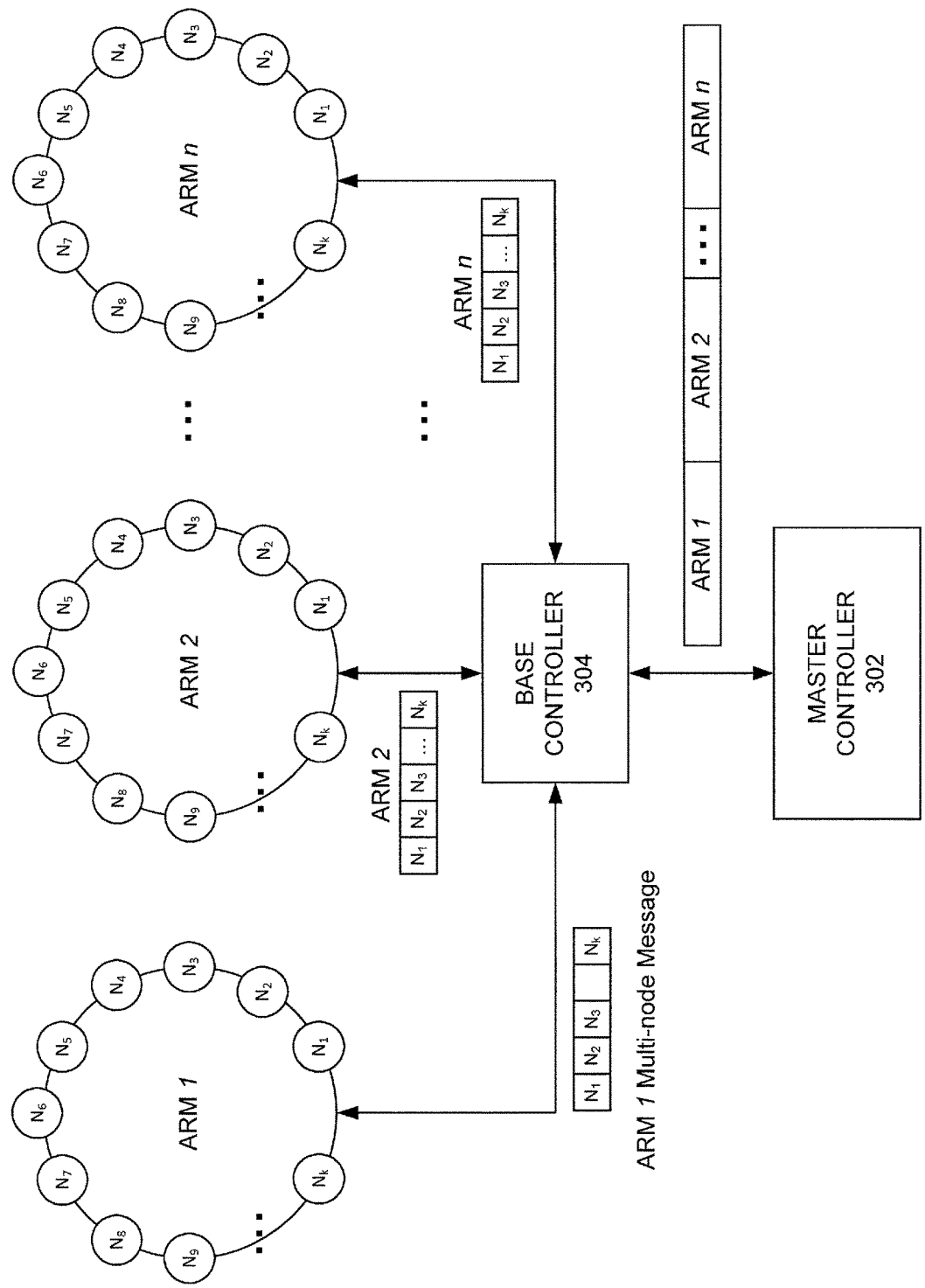
FIG. 3 is an illustration of a communications network of a robotic surgical system of an embodiment.

Returning to the drawings, FIG. 3 is an illustration of a communications network of a robotic surgical system of an embodiment. As shown in FIG. 3, the robotic surgical system of this embodiment comprises a master controller 302 (sometimes referred to herein as "the robot controller" or "the data master" or simply "the controller") in communication with a base controller 304 (sometimes referred to herein as "the second controller"), which is in communication with a plurality of robotic arms (ARM 1-ARM n). As used herein, the phrase "in communication with" could mean directly in communication with or indirectly in communication with through one or more components, which may or may not be shown or described herein. For example, signals from the master controller 302 and base controller 304 can be communicated to the nodes through wired connections bundled (e.g., in a wire harness) passing within the internal volumes of the arm links and joint modules of the robotic arm. Also, it should be noted that while FIG. 3 shows a plurality of robotic arms, a robotic surgical system can have only a single robotic arm, in which case the base controller 304 may not be used. In some embodiments, the base controller 304 is not used even when the robotic surgical system has a plurality of robotic arms. In one embodiment, base controller 304 is located in or near the patient table or bed (in such situations, the base controller 304 may be referred to as the table adapter controller ("TAC")), and the master controller 302 is located in a communication tower separate from the patient bed.

It should be noted that any of the controllers can be implemented in any suitable manner. For example, a controller can take the form of processing circuitry, a microprocessor or processor, and a computer-readable medium that stores computer-readable program code (e.g., firmware) executable by the (micro)processor, logic gates, switches, an application specific integrated circuit (ASIC), a programmable logic controller, and an embedded microcontroller, for example. A controller can be configured with hardware and/or firmware to perform the various functions described below and shown in the flow diagrams. More generally, a controller (or module) can contain "circuitry" configured to perform various operations. As used herein, the term "circuitry" can refer to an instruction processor, such as a Central Processing Unit (CPU), microcontroller, or a microprocessor; or an Application Specific Integrated Circuit (ASIC), Programmable Logic Device (PLD), or Field Programmable Gate Array (FPGA); or a collection of discrete logic or other circuit components, including analog circuit components, digital circuit components or both; or any combination thereof. Circuitry may include discrete interconnected hardware components or may be combined on a single integrated circuit die, distributed among multiple integrated circuit dies, or implemented in a Multiple Chip Module (MCM) of multiple integrated circuit dies in a common package, as examples. Accordingly, "circuitry" may store or access instructions for execution or may implement its functionality in hardware alone.

The master controller 302 can receive commands from the user console 100 (FIG. 1) for manipulating the robotic arms and transmit those commands to the robotic arms. As shown in FIG. 3, in this embodiment, the nodes of each robotic arm are arranged in a ring network. As used herein, a ring network refers to a network topology in which each node connects to two other nodes, forming a single continuous pathway for signals through each node. Data travels from node to node, with each node along the way handling every packet. The propagation delay may be balanced, especially for the nodes at the distal end of the robotic arm. While FIG. 3 shows that each robotic arm has the same number of nodes, in other embodiments, at least one robotic arm has a different number of nodes than another robotic arm in the system. As will be discussed in more detail below, the ring network can be used for communicating both real-time and asynchronous information across the robotic arm network.

The master controller 302 is configured to communicate with the plurality of nodes in a given robotic arm using a multi-node message comprising a plurality of packets, each packet associated with a different node in the robotic arm. The arm multi-node message is "multi-node" in that it can comprise data for all the nodes on that arm. A packet can be associated with a node in any suitable way. For example, each packet can be addressed to a different node (e.g., using an identifier of the node) in the robotic arm and/or a node can be associated with a particular packet position in the message. Of course, these are just examples, and other associations can be used.

Figure 4:
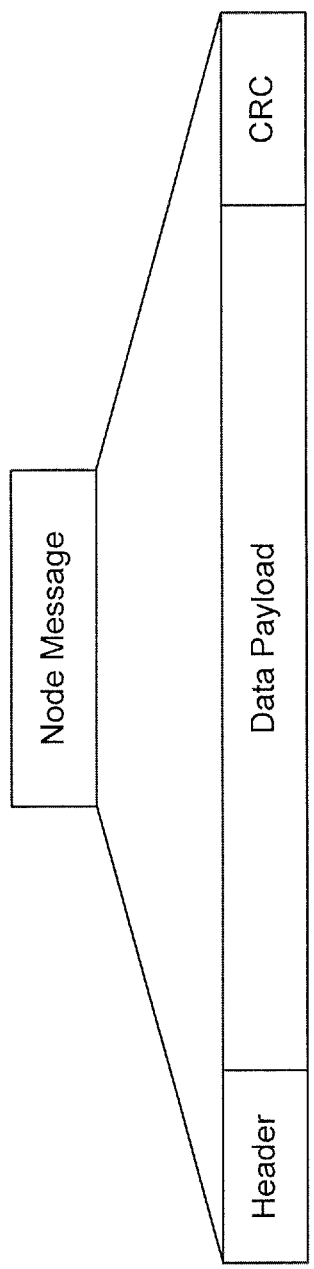

Each packet in the multi-node message can be formatted in any suitable manner. For example, as shown in FIG. 4, in one embodiment, a packet in the multi-node message can contain a header, a data payload, and a cyclic redundancy check (CRC) field. In another embodiment shown in FIG. 5, the packet comprises a 16-bit packet framing constant, a 16-bit header, a fixed size (e.g., 128-bit or 224-bit) data payload including cyclic data (command or feedback), non-cyclic, and asynchronous data, and a 16-bit CRC field (e.g., CCITT). The packet framing constant can be used to confirm the start of the packet. The payload data type can be used to determine the format of the data payload (e.g., motor command, motor feedback, digital inputs, digital outputs, and force feedback). The channel ID can be used by a node to confirm that the packet is intended to be delivered to that node. (In one embodiment, all the nodes across all the robotic arms have a unique channel ID.) The sequence field helps a node determine whether the packet is new or not. The master controller 302 increments the sequence number every time it sends out a new packet. If the master controller 302 gets interrupted, a node would see the same sequence number twice and know it is a duplicate packet. The CRC field can cover the entire packet. In one embodiment, there are 80 packets per frame, with each frame being the same size. Of course, this is just one example, and other configurations can be used.

If only one robotic arm is used, the master controller 302 can send the multi-node message directly to that arm. If multiple robotic arms are used, the master controller 302 can send all of the multi-node messages for all the arms together in a single message to the base controller 304. The base controller 304 can separate out each individual multi-node message from the single message and send each robotic arm its associated individual multi-node messages. For example, the base controller 304 can route messages to different robotic arms based on the message's offset in the overall combined message.

After the multi-node messages pass through the ring and return to the base controller 304, the base controller 304 can combine the received individual multi-node messages into a single returned merged message, and send the single returned merged message to the master controller 302. The base controller 304 can be configured to perform other functionality. For example, the base controller 304 can be used to move the robotic arms if the master controller 302 is not plugged into the system (e.g., allowing a nurse to move the robotic arms out of the way before draping the patient).

As mentioned above, the multi-node message is used to communicate with the nodes in a given arm. A multi-node message resembles a train with k boxcars, each node on the arm is assigned a boxcar, and passengers (data payload) get on and off their designated boxcar (i.e. full-duplex). The master controller 302 can schedule one or more multi-node messages per cycle, and timing of each message can be optimized for optimal control of a distributed, digitally-sampled system.

Figure 6A:
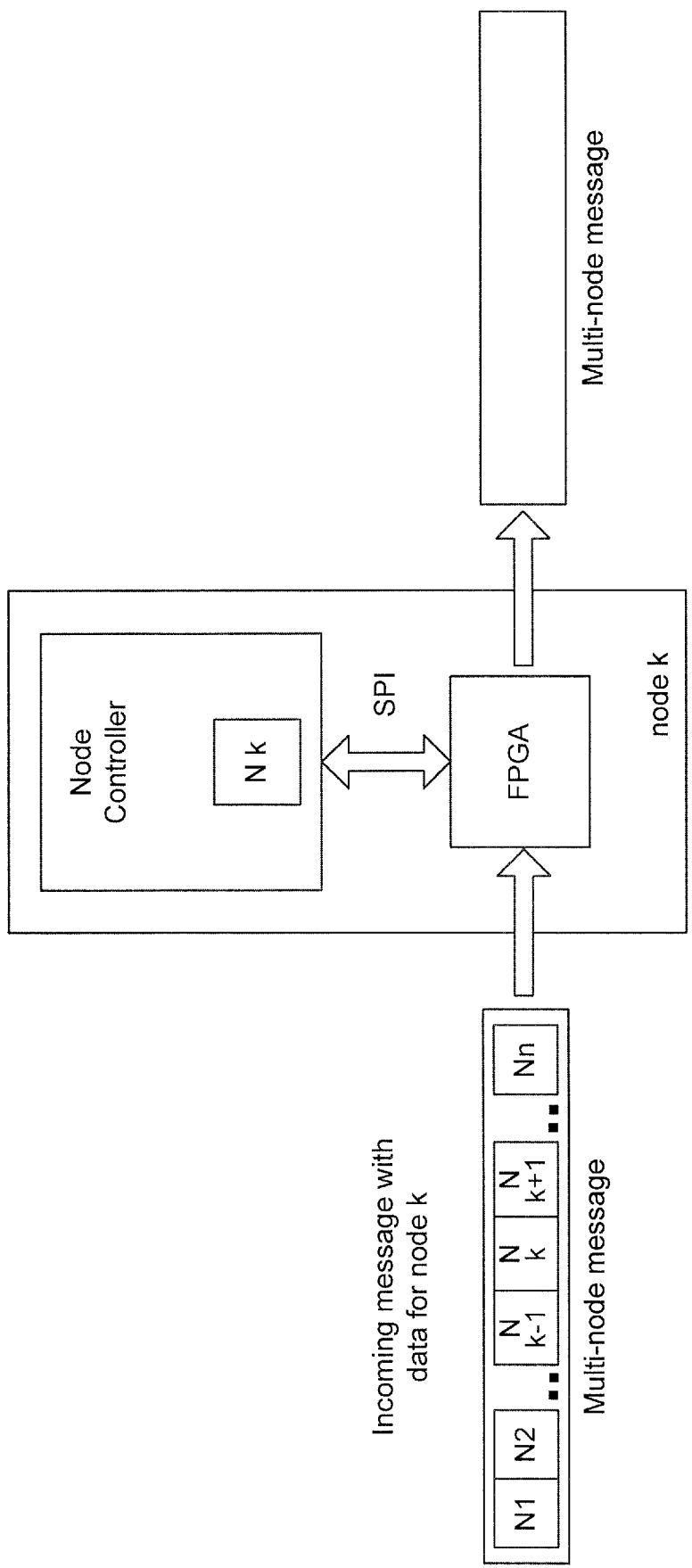
FIGS. 6A, 6B, and 6C are illustrations of an on-the-fly node message exchange of an embodiment.
Figure 6B:
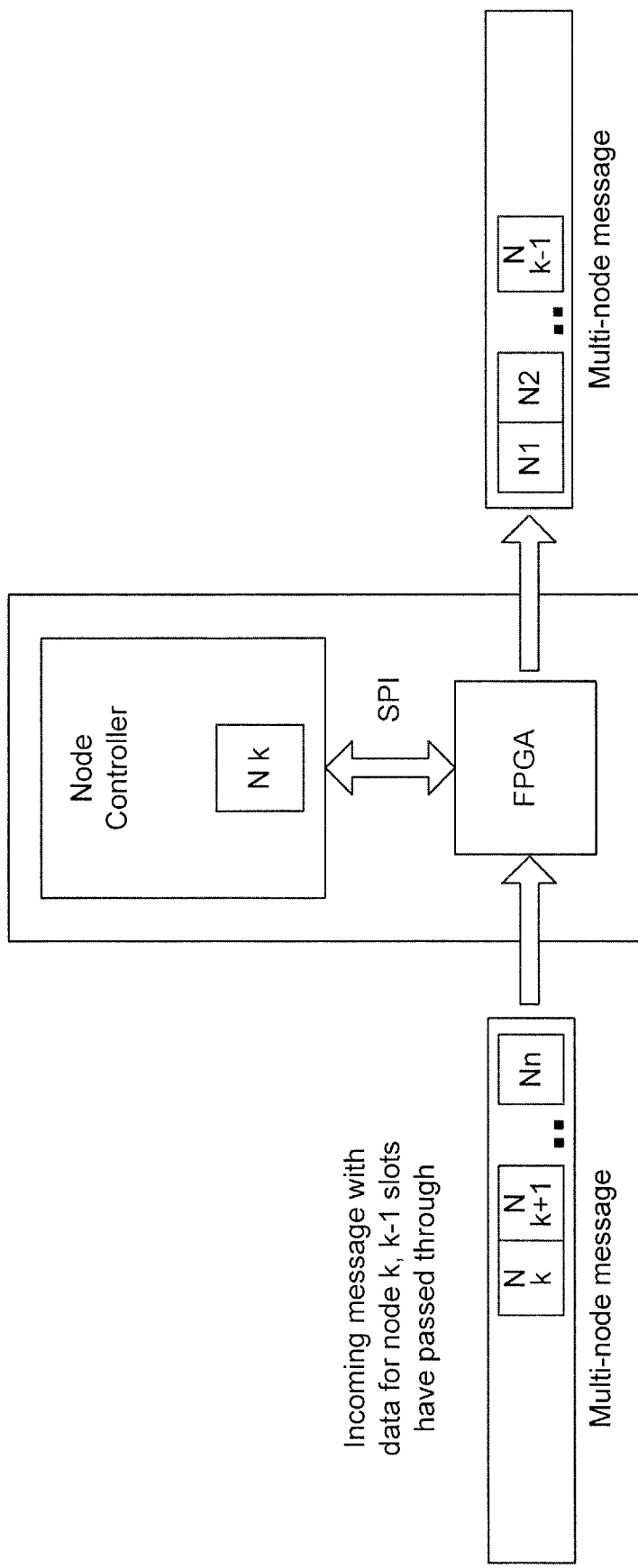
Figure 6C:
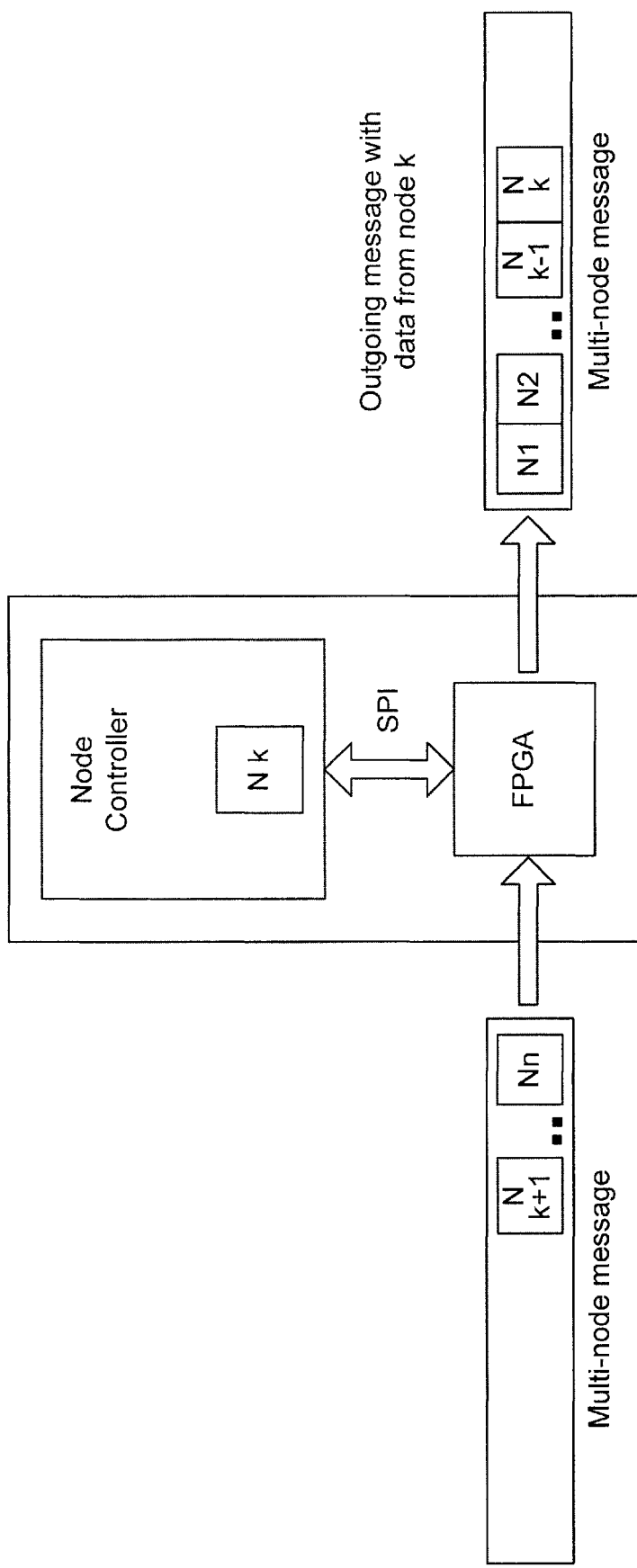

FIGS. 6A, 6B, and 6C illustrate this communication flow. As shown in these figures, a node can comprise a field-programmable gate array (FPGA) that processes a multi-node message and is the physical interface between the node and the ring network. In one embodiment, the FPGA and the node controller communication via a serial peripheral interface (SPI) bus. Although not shown to simplify the drawings, a node can have one or more additional components, such as a motor or sensor, connected to the node controller.

In operation, the FPGA decodes the multi-node message, looks for the synch token, and determines which packet in the message is associated with the node. It can then exchange data in a packet of the message. For example, as shown in FIGS. 6A and 6B, after the FPGA receives a message, it lets packets of the message pass through until the FPGA determines that a given packet is associated with its node. As shown in FIG. 6C, at that time, the FPGA can copy the data from the packet to a memory in the node controller and swap in other data stored in the memory of the node controller. The swapped-in data can be prepared in advance by the node controller, so it is ready to be sent once the appropriate packet arrives. In this embodiment, the SPI bus uses a protocol that does an automatic exchange, and the FPGA can be programming with a slight delay to account of any synchronization issues in moving data out of and into a packet. The net effect of this is that there is very little latency being introduced by each node because each node is receiving and responding to its packet at the same time as other nodes (i.e., each node is not receiving the whole multi-node message and then sending a response).

In one embodiment, by default, all messages in the multi-node message are passed through any node unaltered. A node is programmed to extract and replace only specific messages based on programmed start values relative to the frame sync token and a programmed message length. This is the analogy of a node being assigned a specific railroad car within the train (or rather two as there are two exchanges per frame). If there are n nodes, then there are 2n cars, and node x will be assigned cars x and x+n. In one embodiment, each node must exchange data at the allotted times, and failure to do so is a system fault (other implementations are possible). The node may be required to generate properly-formatted response packets even if no new data is available. As mentioned, there are two data exchanges per frame, carrying synchronous commands/asynchronous responses and asynchronous commands/synchronous responses, respectively. Data exchanges are based purely on the position of a message relative to the sync token. Any interpretation of the message itself is done inside the processor during the time between messages. Likewise, any responses are prepared by a node prior to the arrival of the transmission time slot. A node is responsible for making sure that it can meet the timing required for this.

Examples of Communicating Synchronous and Asynchronous Information to and from Nodes of a Robotic Arm In one embodiment, the information to be communicated between the master controller 302 and the nodes of a robotic arm can be generally classified as "synchronous information" or "asynchronous information." As used herein, "synchronous information" refers to information that is intended to be processed upon receipt or within a certain timeframe (in real time), whereas "asynchronous information" refers to information that can be stored and processed later (without the requirement that it be processed within a certain timeframe). So, as compared to synchronous information, there can be some latency between when asynchronous information is received and when it is processed. For example, a command to actuate a motor can be classified as synchronous information because a surgeon expects the robotic arm to move immediately after instructing the movement. As such, the command needs to be performed within a certain timeframe. In contrast, a command that performs a low-priority maintenance function can be classified as asynchronous because the command does not need to be performed under a strict timeframe and can be performed whenever the node gets around to it.

In one embodiment, the timing of transmission between the master controller 302 and nodes of a robotic arm is the same irrespective of whether the information being conveyed is synchronous information or asynchronous information. Accordingly, "synchronous" and "asynchronous" refers to an information type on the protocol level (i.e., whether or not a command needs to be processed in real time) and not to a timing requirement on the transport level, as both synchronous information and asynchronous information have the same transport synchronicity in this embodiment. In one embodiment, the only difference between asynchronous and synchronous with respect to timing is that the latter has slightly lower latency due to placement within a frame.

Any suitable type of synchronous information and asynchronous information can be used and can take the form of commands (sometimes referred to as "requests") and responses to commands. For example, a synchronous command can be a command (i.e., a real-time motor control command) sent to a node that, when processed/executed by the node, actuates a motor to move a link in the robotic arm to a certain position or exert a specific torque. A response from the node to the synchronous command can be feedback to that command (e.g., a reading from a force/torque sensor in the node to confirm that the requested movement actually occurred). An asynchronous command can be a command sent to a node to request information from the node (e.g., identification of a surgical tool plugged into the robotic arm and information on its calibration and kinematic parameters), to request that a supervising/housekeeping function be performed (e.g., measuring temperatures and voltages of a node), or to request a change to one of the node's parameters.

As noted above, in one embodiment, the timing of transmission between the master controller 302 and nodes of a robotic arm is the same irrespective of whether the information being conveyed is synchronous information or asynchronous information. The following paragraphs describe a protocol of an embodiment that can be used to schedule synchronous information or asynchronous information on a real-time network. This real-time protocol can be used to prescribe data transfer and data sequences between the master controller 302 and distributed motor controllers in the nodes of a robotic arm, for example. With such a protocol, a lightweight, deterministic communication system can be tightly-integrated into the robotic platform, providing a robust and maintainable design.

In general, the communications protocol of this embodiment provides real-time isochronous data communication of synchronous and asynchronous information using statically-allocated bandwidth and a simple schedule for sharing the bandwidth among different types of synchronous and asynchronous information. In one embodiment, the communication protocol uses a constant cycle time to support hard, isochronous real-time data transfer between the master controller 302 and the plurality of nodes in the robotic arms. (As used herein, a cycle can refer to the time from when the master controller 302 sends one or more multi-node messages to the ring network to when it receives those message(s) back from the ring network.) Although any suitable cycle time can be used, in one embodiment, the cycle time is at a high frequency (e.g., 4 kHz) that can provide a motion control update rate with minimum latency and minimum jitter. As will be discussed in more detail below, in one embodiment, payloads of the data packets alternate between synchronous commands (e.g., motor control commands), asynchronous commands, responses to synchronous commands (e.g., sensor feedback), and responses to asynchronous commands. In this embodiment, each category of data receives a fixed fraction of the total bandwidth and is served with the same priority as other categories of data.

Figure 7:
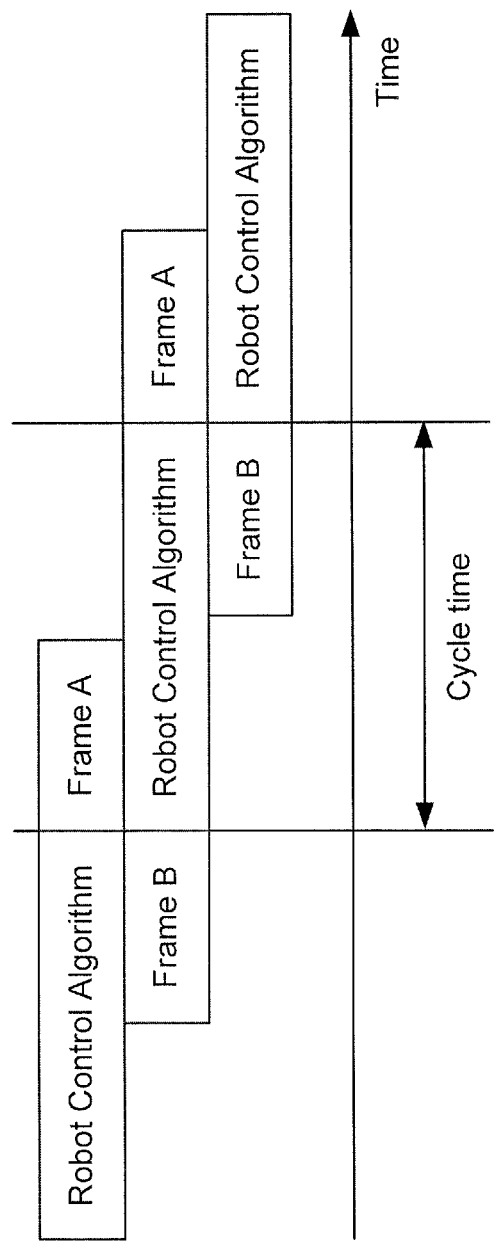
FIG. 7 is an illustration of a communications protocol of an embodiment.

As noted above, in one embodiment, cycle time is constant (nominally, 250 microseconds) to support isochronous real-time data transfer with a hard deadline for communication, and two frames of data are exchanged each cycle. This is illustrated in FIG. 7. As shown in FIG. 7, in a given cycle, two frames of data are being transmitted between the master controller 302 and the nodes of the robotic arms. At the same time, the master controller 302 is executing a robot control algorithm to determine what commands to issue in the next command cycle. For example, looking at the center line in FIG. 7 from left to right, in the first communication cycle, the master controller 302 receives Frame B, which contains, in this example, the sensor data coming the motor controllers in all of the arms (i.e., responses to synchronous commands previously received by the nodes). In the second communication cycle, the master controller 302 uses that sensor data to determine what command to send to the nodes in the next communication cycle. For example, if the sensor feedback shows that the robotic arm is not in the intended position, the master controller 302 can determine that another motor command is needed for that node to correct position. In the third communication cycle, the master controller 302 sends Frame A, which contains the commands determined in robot control algorithm in the previous cycle, to the nodes. Accordingly, this communication protocol uses pipelining and staging. As such, actions overlap in time, and there is certain amount of latency from when the feedback is received to when a new command is being sent out.

Figure 8:
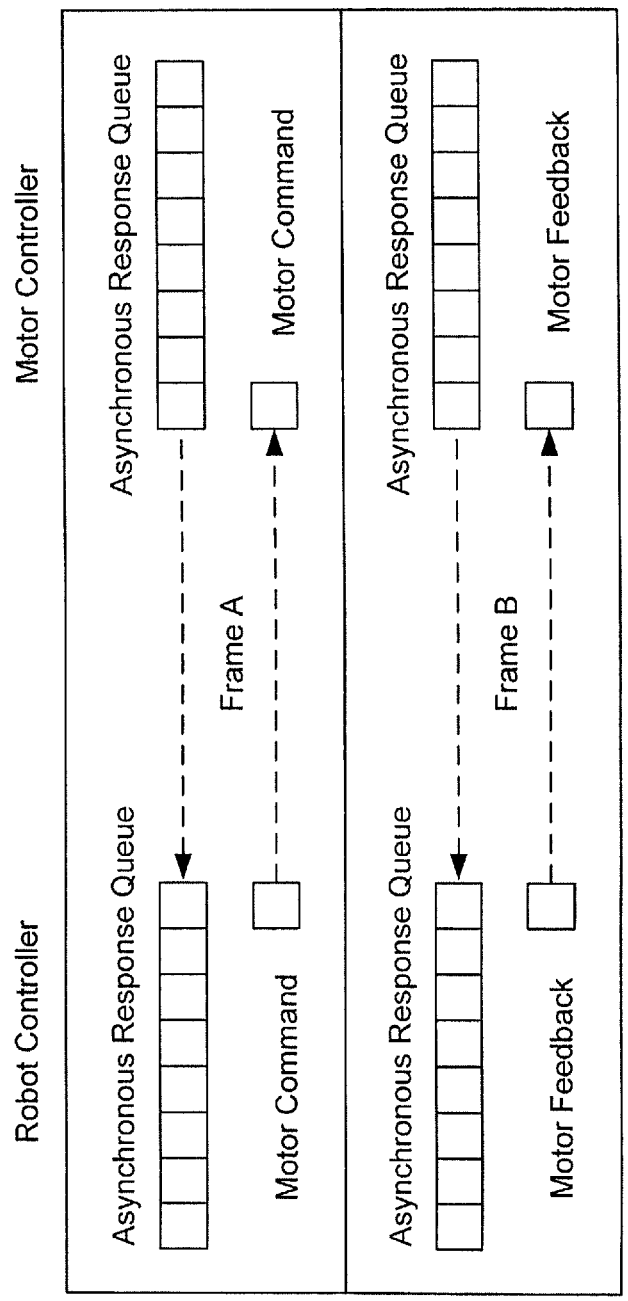
FIG. 8 is an illustration of how synchronous information and asynchronous information are communicated in a robotic surgical system of an embodiment.

Turning now to FIG. 8, FIG. 8 shows how the two frames in a cycle can be used to communication synchronous information between the master controller 302 (called a "robot controller" in this example) and a node (a motor controller in this example). As shown in FIG. 8, during one part of the cycle (Frame A), synchronous commands (e.g., motor commands) are sent from the master/robot controller 102 to each node (e.g., motor controller), and responses to asynchronous commands received in an earlier cycle are sent from each node to the master/robot controller 302. During another part of the cycle (Frame B), a response to a synchronous command received in an earlier cycle (e.g., motor feedback in response to a motor control command) is sent from each node to the master/robot controller 302, and asynchronous commands are sent from to the master/robot controller 302 to each node. Accordingly, in every frame, asynchronous information is interleaved with synchronous information. That is, for each frame, half the bandwidth is reserved for asynchronous information, and the other half of the bandwidth is reserved for synchronous information.

As noted above, while synchronous information is processed in real time, asynchronous information (commands or responses) can be stored and processed at a later time. As asynchronous information may not be consumed in real time, FIG. 8 shows that the master/robot controller 402 and a node (such as a motor controller) can have at least one memory to queue asynchronous commands (requests) and responses to be sent or processed. In this way, the queues create a buffer between what is happening in the asynchronous domain and what is happening on the real-time network. For example, the master/robot controller 402 can generate asynchronous housekeeping commands and store them in an asynchronous request queue until it has the opportunity to send them out to the nodes. Likewise, the node can store an asynchronous housekeeping command in its queue and can get around to processing it when the node has a chance. The same queue process of the node and master/robot controller 302 can occur when the node sends asynchronous responses to the master/robot controller 302. However, as shown by the single boxes in FIG. 8, synchronous commands/responses are sent and acted upon in real time (i.e., they are not stored for transmittal and execution at a later time).

With reference again to FIGS. 7 and 8, in one embodiment, the synchronous feedback occurs as late in a cycle (cycle N−1) as possible, so that the robot control algorithm has the most up-to-date information as it is deciding (in cycle N) what the next synchronous command for the next cycle (N+1) should be. Also, in one embodiment, the synchronous command is sent as early in cycle N+1 as possible, so the synchronous command can reach its node and be executed as soon as possible.

Examples of a Physical Layer of a Communication Network of a Robotic Surgical System Any suitable physical layer can be used in the network. In one embodiment, communication between the base controller 304 and the nodes on the robotic arm uses a twisted-pair copper cable with pseudo-low-voltage differential signaling (LVDS) with additional low speed bi-directional common mode communication capabilities. To minimize the longest cable length, instead of using a single cable to connect all the nodes to the base controller 304, short cables can be used between each component. These features are shown diagrammatically in FIG. 9.

Communication between the master controller 302 and base controller 304 can use a fiber optic link to achieve electrical isolation and low electromagnetic interference. In one example implementation, a fiber optic link that is compatible with 1000 BASE-SX Ethernet is used. However, the link does not carry Ethernet packets, but rather uses an Aurora interface with a 1.25 Gbps raw bit rate. This implementation can provide advantages to other types of solutions. For example, a Controller Area Network may be too slow for certain requirements (e.g., 1M bit/s, 400 Hz cyclic rate), Ethernet is not suitable for real-time communication and is too big and heavy, and Ethernet for Control Automation Technology (EtherCAT), while supporting hard real-time applications, can be too big and expensive of a solution for some applications.

As mentioned above, to minimize the longest cable length, instead of using a single cable to connect all the nodes to the base controller 304, short cables can be used between each component. The following paragraphs describe a ring topology that equalizes node-to-node length, allows replacement of individual nodes easily, and (optionally) does not allow reversed connectors.

For real-time control, a high-speed bus is desirable. However, ring topologies that are mechanically in a linear fashion typically have short hops between nodes and a long return path, which decreases the maximum speed of the bus. The long return is also more susceptible to noise. Having two connectors at each node also lends itself to reversing transmit and receive cables, which is not ideal. The typical wiring in a node-skipping configuration would have wires not terminated at each node and replacing a node would require disassembling the two adjacent nodes.

Equalizing the distance between each node allows for a higher bus speed and distributed noise. There are two visible communication cables at each node, so knowing where each one connects is beneficial from a manufacturing and reducing troubleshooting point of view. The typical wiring in a node-skipping configuration would have wires not terminated at each node. Replacing a node would require disassembling the two adjacent nodes as well. The terminations on the pass-through take care of this issue.

Figure 13:
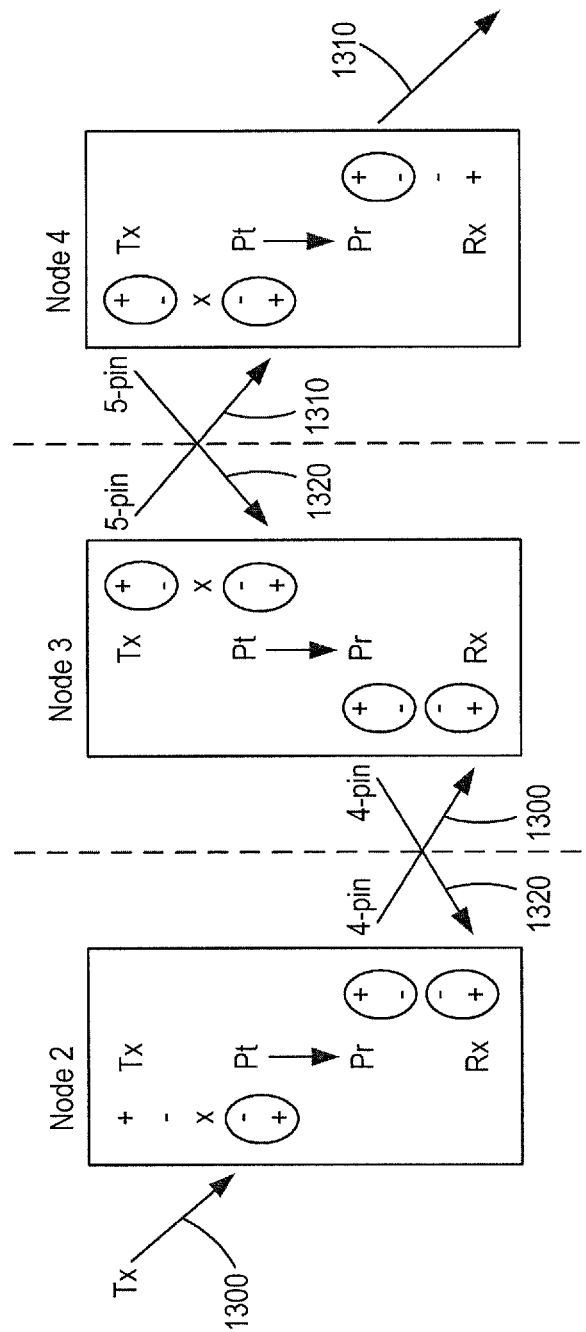
FIG. 13 is a diagram of a non-reversible equalized node-disconnectable ring wiring topology of any embodiment.

With reference to FIG. 13, in one embodiment, each node has pass-through cable connectors and active cable connectors, which can be used to provide a node-skipping configuration. More specifically, in one embodiment, each node has two unique connector cables wired as crossovers (pin 1 wired to pin 4, pin 2 to pin 3, etc.). In one implementation, one cable is 4-pin to 4-pin, and the other is 5-pin to 5-pin. The use of these two different connectors prevents reversed connections. The 4-pin cable connects the pass-through to receive signals from the adjacent nodes. The 5-pin connects to the pass-through on the adjacent nodes. The pass-through is local to each node. Accordingly, each node comprises pass-through cable connectors and active cable connectors, so that the cables can be connected to the pass-through cable connectors and the active cable connectors to provide a node-skipping configuration. This is illustrated in FIG. 13. As shown in FIG. 13, arrows 1300 show the increasing node number part of the ring, and arrows 1310 show transmit from Node 3, passing through Node 4, and received by Node 5. Arrows 1320 show the decreasing node number part of the ring where a transmit signal from Node 4 passes though Node 3 and is received by Node 2. This can be thought of as an "out and back," where half the nodes are active on the way out, and the remaining half are active on the way back.

The loopback can either be local on the last node or through an external loopback cable on last node. In one embodiment, the last node is only physically the last node in the linear layout; it is actually the n/2 node in the data flow layout. The first node or "master" can have both transmit and receive without a loopback.

Figure 9:
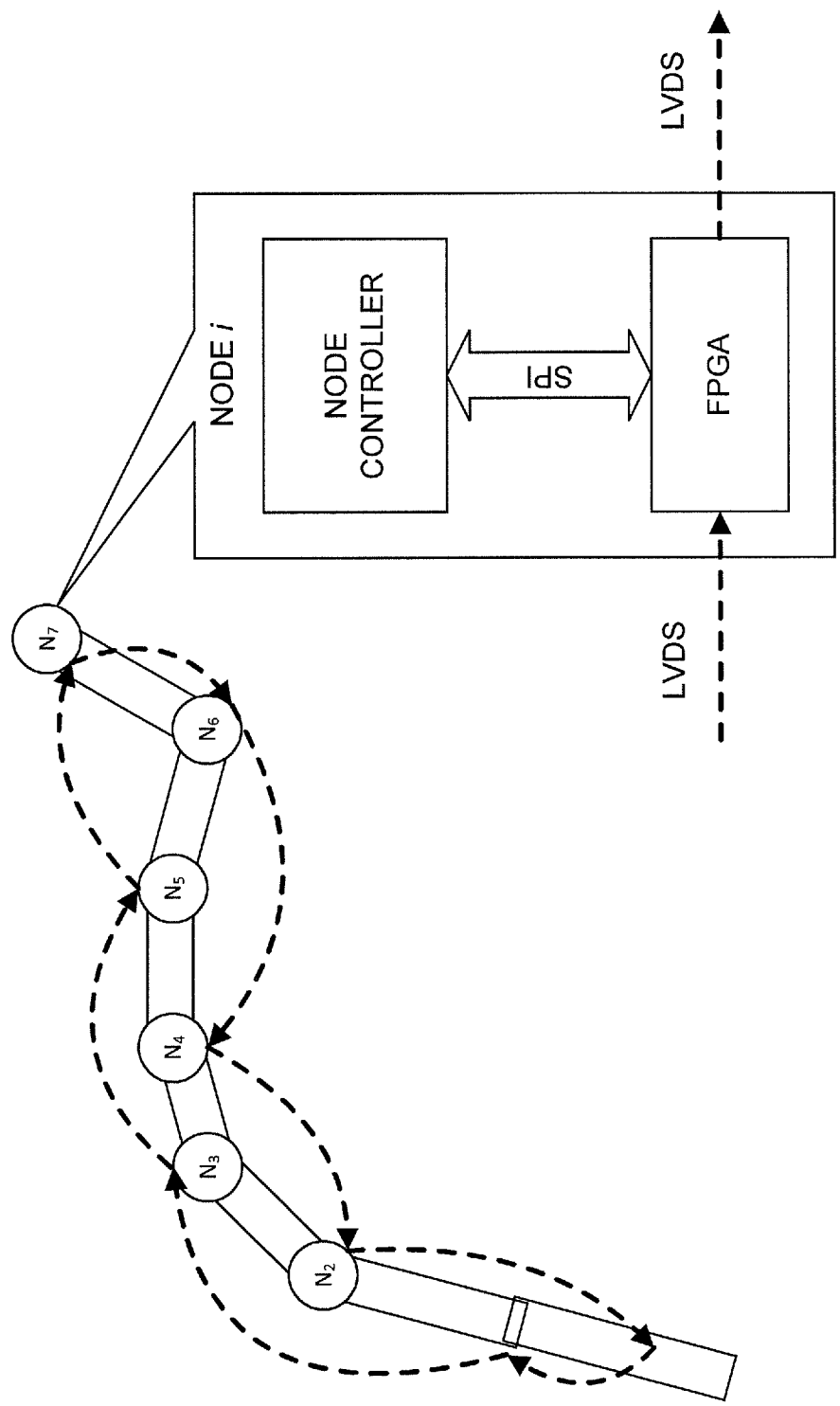
FIG. 9 is a block diagram illustrating communication into and out of a node on a network of a robotic surgical system of an embodiment.

Also, in one embodiment, the base controller 304 is the timing master for the communication with the nodes. This will be discussed in conjunction with FIG. 10, which is another view of the ring network of an embodiment. As discussed above, the base controller 304 can separate out each individual multi-node message from the single message and send each robotic arm its associated individual multi-node messages simultaneously. In this embodiment, the base controller 304 is responsible for timing the communications to the nodes, so that simultaneous communication occurs. For example, as shown in FIG. 9, between $t_0$ and $t_1$, a first byte of each multi-node message is transmitted to each destination arm at the same time. Similarly, in the opposite direction, returned messages from the arms are assembled simultaneously into the master merged message.

Figure 10:
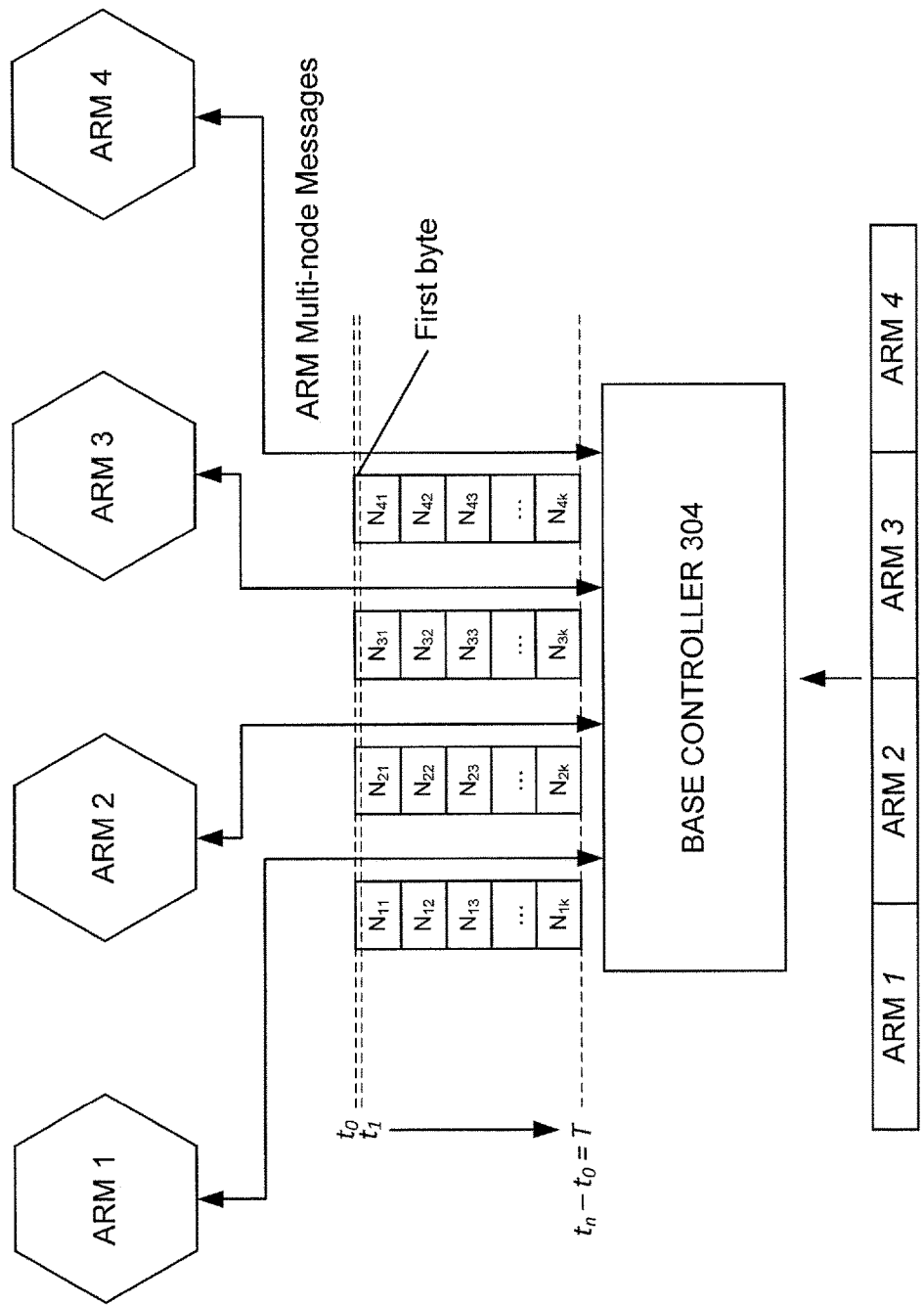
FIG. 10 is an illustration of a communications network of a robotic surgical system of an embodiment.

In one embodiment, in addition to being responsible for separating out various multi-node arm messages, the base controller 304 is responsible for timing and scheduling the communications. The base controller 304 is the "timing master" in that it can generate the 4 KHz frame and know when to send the messages to and receive the messages back from the robotic arms (e.g., so the messages are sent to/received from the nodes at the same time). For example, as shown in FIG. 10, in one cycle (T), there can be $t_n$ slots (or "unit intervals (UI)"). At a 4 KHz cycle time, there can be 15,000 unit intervals ($t_0$ plus $t_n$) (assuming a 60 Mbps UI rate). The base controller 304 can know exactly how many unit intervals get transferred per cycle and because communication on the network is isochronous communication, the base controller 304 can communicate the clock to the nodes on the network, so they can lock in their local clock to the master clock. In one embodiment, each node has a phased-locked loop (PLL) that can be regenerated with the master clock. In this way, all the nodes in the network can run at the same frequency (e.g., by setting the integer fraction relationship to the 250 us frame period in this example), so they do not wander relative to one another. In another example, the PWM runs at 40 kHz, i.e., 10 times faster than the 250 us frame rate.

Figure 11:
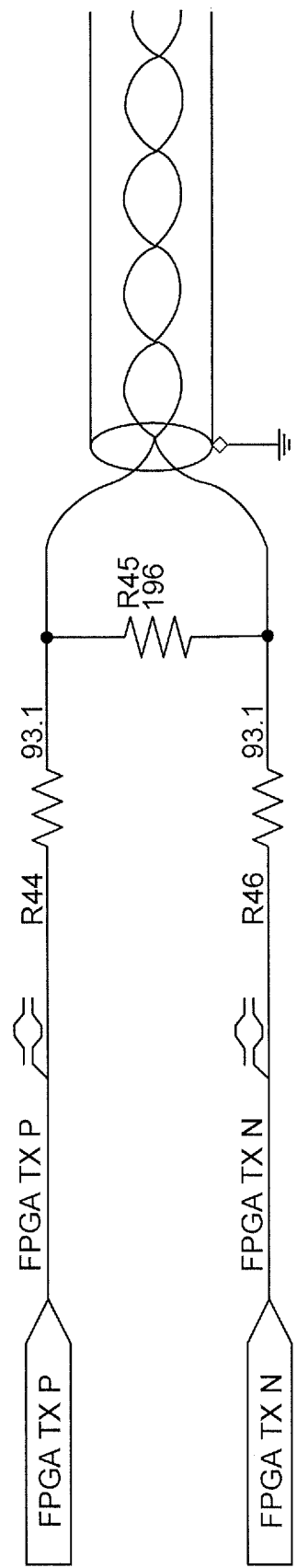
FIG. 11 is an illustration of a transmitter of a network component of a robotic surgical system of an embodiment.
Figure 12:
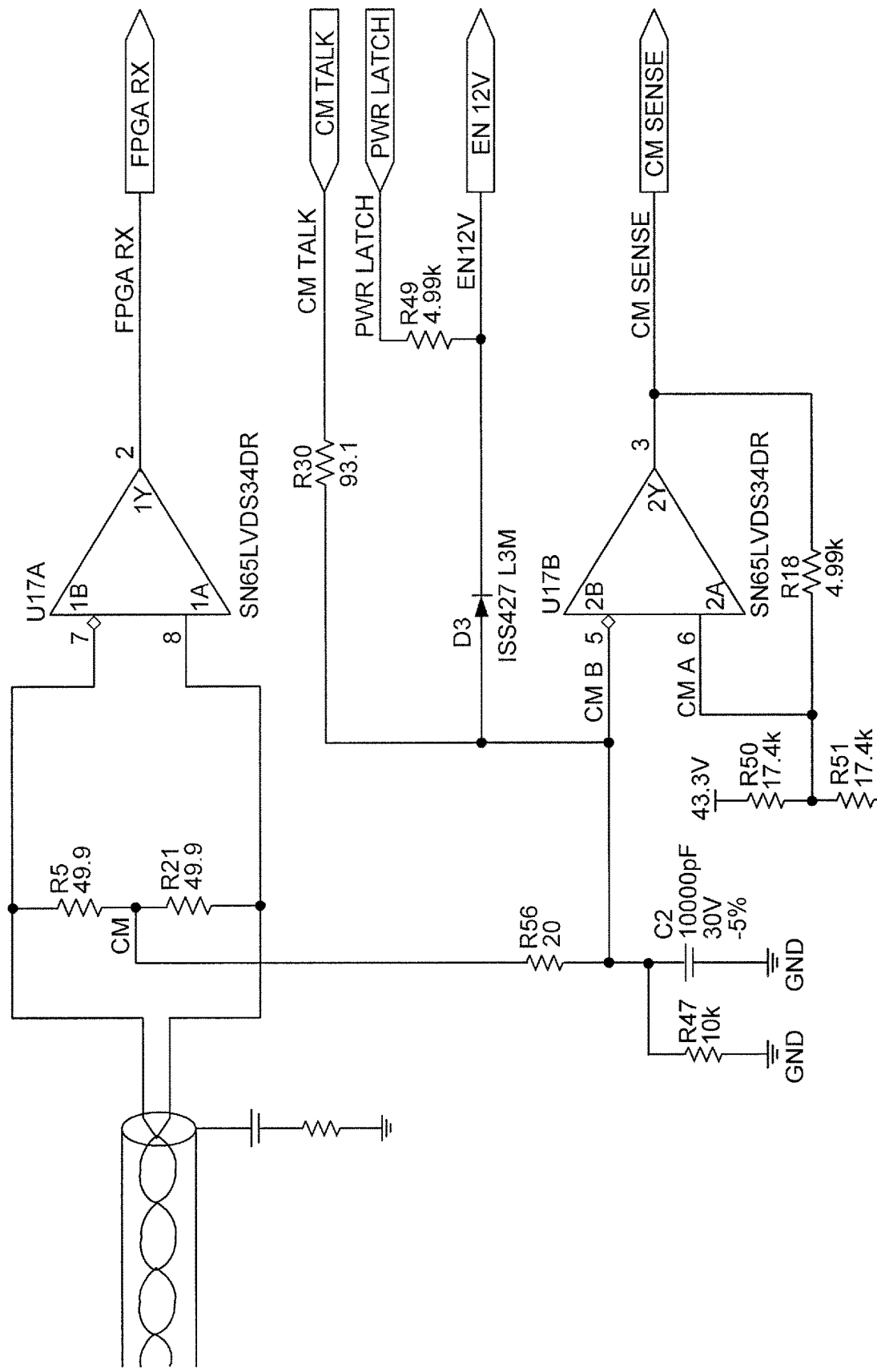
FIG. 12 is an illustration of a receiver of a network component of a robotic surgical system of an embodiment.

FIGS. 11 and 12 are illustrations of a transmitter and a receiver that can be used to communication on the physical network between the base controller 304 and the nodes on the robotic arm. It should be noted that this is just one example, and other configurations can be used. Turning first to the transmitter in FIG. 11, the transmitter in this embodiment is a "pseudo-LVDS" transmitter, in that the outgoing signal is compatible with LVDS, but it is not transmitted by a conventional LVDS transmitter. There are a few reasons for this. For example, LVDS is typically around 1.25 volts in common mode, going up or down a couple hundred millivolts to transmit 0 s and 1 s. The transmitter in this embodiment generates the same signal leveling through an external resistor divider. Driving one input high and the other low results in a signal that is LVDS compatible. Driving both inputs high or low results in low results in a common mode of 3.3 volts and 0 volts, respectively, which can be used to encode additional information (e.g., for power-up sequencing and for a secondary low-speed communication channel to initialize the ring network). Another reason for using this pseudo-LVDS transmitter is to provide a back-terminated transmission line, so if there is any noise on the line, it will die down in half its delay time and does not have to bounce back and forth. Specifically, in this embodiment, 3.3V LVCMOS outputs are wired through a resistor network to produce a back-terminated 100 Ohm differential drive into a shielded twisted pair. For reverse direction communication, the drivers are disabled and used as inputs to sense the common mode line voltage.

Turning now to the receiver in FIG. 12, the receiver in this embodiment contains a high common mode range LVDS receiver for a high speed interface and a low pass filtered common mode voltage detector with hysteresis. In addition, the receiver can drive the common mode voltage (via CM_TALK) for upstream communication. The arm motor nodes additionally contain circuitry that senses the common mode voltage to turn on the nodes after a power-up. This is meant to be used to stagger the in-rush currents inside the arm. Once powered, the enable is latched, and the node remains on. More specifically, the receiver in this embodiment has a LVDS receiver with high common mode rejection capabilities, which means it can differentiate the small differential signal in the presence of a large, common mode voltage. The top section of the receiver of this embodiment can handle a situation where there is a noise spike (e.g., when a motor is activated and partially collapses the power supply) and the ground reference between the nodes swing arounds. The receiver of this embodiment has common mode rejection capability to still be able to reliably detect low voltage differences in the presence of common mode.

The bottom section of the receiver of this embodiment can distinguish the common mode signal. So, if the transmitter is driving both input signals high or low, the bottom section of the receiver can detect using a comparator with a large amount of hysteresis for noise suppression. Above that comparator is a diode to power up the nodes in sequence to avoid large rush currents that may be difficult for the power distribution network to sustain. In particular, one embodiment isolates the power for each arm for safety reasons. So, when the arm is powered up, the voltage is there, but the individual regulators in the nodes are not actually turned on yet because common mode 0 is driven on the ring network (so, the voltage on EN 12V will be low). The node that is in the base of the arm is first driven to common mode high, which will then go through that diode and turn on the regulator for the next node. One embodiment uses an automatic delay of about 5 milliseconds, as the delay can allow all in-rush currents to subside before the output driver is high. Rippling the power through the nodes in this way staggers the powering on of the nodes and distributes in-rush currents over a longer period of time and makes them smaller. The receiver of this embodiment also has a CM Talk signal to provide the receiver with the capability to talk to the transmitter. So, the transmitters can be turned off and turned around as inputs for debugging and diagnostic purposes.

As mentioned above, while communication between the base controller 304 and the nodes is through pseudo-LVDS using twisted-pair copper cable in one embodiment, communication between the master controller 302 and base controller 304 can use a fiber optic cable. In one embodiment, the master controller 302 has a computer with a PCIE card for communicating with the fiber optic cable. The master controller 302 receives timing signals from the base controller 304 and is responsible for sending out synchronous and asynchronous commands to the base controller 304 for distribution to the nodes of the robotic arms.

As explained above with reference to FIGS. 7 and 8, in one embodiment, the synchronous feedback occurs as late in a cycle as possible, so that the robot control algorithm has the most up-to-date information as it is deciding what the next synchronous command should be. Also, in one embodiment, the synchronous command is sent as early in a cycle as possible, so the synchronous command can reach its node and be executed as soon as possible. That is, this embodiment attempts to minimize the latency between when the master controller 302 receives feedback from the nodes and when it sends out the new real time commands to the nodes by phase-shifting the base controller 304—arm communications with respect to the master controller 302—base controller 204 communications. The master controller 302 can be responsible for this timing. As these transmissions inside the master controller 302 are over PCIE, they are very fast and take up only a small section of the 250 microseconds cycle time. Once the data goes out over fiber, the transmission is not as fast as over PCIE, but the data can be interleaved and placed in the proper order, so that the data can be streaming smoothly. That way, the base controller 304 does not need to be responsible for ordering the packets, which can take a relatively significant part of the cycle time.

Finally, it should be noted that the protocol discussed above does not have to occupy all of the bandwidth of the communication link. This allows running additional protocols (e.g., a secondary ("node management") protocol used for initialization and health checks of the system) during the gaps in the ring network communications.

CONCLUSION

It is intended that the foregoing detailed description be understood as an illustration of selected forms that the invention can take and not as a definition of the invention. It is only the following claims, including all equivalents, that are intended to define the scope of the claimed invention. Finally, it should be noted that any aspect of any of the preferred embodiments described herein can be used alone or in combination with one another.

What is claimed is:

1. A robotic surgical system comprising:
a plurality of robotic arms, each robotic arm comprising a plurality of nodes arranged in a ring network;
a first controller; and
a second controller in communication with the ring networks of each of the plurality of robotic arms and with the first controller, wherein the second controller is configured to communicate with the plurality of nodes of a given robotic arm using a multi-node message comprising a plurality of packets, each packet associated with a different node in the given robotic arm;
wherein during one part of a communication cycle between the second controller and the plurality of nodes of the given robotic arm, the second controller is configured to send a synchronous command to each node of the given robotic arm using the multi-node message and each node of the given robotic arm is configured to send a response to an asynchronous command sent to that node in a previous communication cycle; and
wherein during another part of the communication cycle between the second controller and the plurality of nodes of the given robotic arm, the second controller is configured to send an asynchronous command to each node of the given robotic arm using the multi-node message and each node of the given robotic arm is configured to send a response to a synchronous command received by that node in a previous communication cycle;
wherein the first controller is configured to send the second controller a single message comprising a plurality of individual multi-node messages, each individual multi-node message associated with a different robotic arm; and
wherein the second controller is configured to separate out each individual multi-node message from the single message and send each robotic arm its associated individual multi-node message.

2. The robotic surgical system of claim 1, wherein the second controller is configured to send the synchronous command at a beginning of the one part of the communication cycle, and wherein each node of the given robotic arm is configured to send the response the synchronous command from the previous communication cycle at an end of the another part of the communication cycle.

3. The robotic surgical system of claim 1, wherein the communication cycle is defined by a constant cycle time to support isochronous real-time data transfer.

4. The robotic surgical system of claim 1, wherein the second controller is further configured to receive individual multi-node messages from the ring networks of each of the robotic arms, combine the received individual multi-node messages into a merged message, and send the merged message to the first controller.

5. The robotic surgical system of claim 1, wherein the plurality of nodes include at least one node having one or more of the following components: a node controller, a single motor, a dual motor, a wireless tool interface, a force/torque sensor, and an input/output board.

6. The robotic surgical system of claim 1, wherein the synchronous command comprises a motor command and the response to the synchronous command comprises feedback regarding performance of a motor command.

7. The robotic surgical system of claim 1, wherein the asynchronous command comprises a request and the response to the asynchronous command comprises a response to a request.

8. The robotic surgical system of claim 1, wherein the second controller comprises at least one memory configured to store asynchronous commands to be sent to the plurality of nodes of the given robotic arm and responses received from the plurality of nodes of the given robotic arm, and wherein each of the plurality of nodes of the given robotic arm comprises at least one memory configured to store asynchronous responses to be sent to the second controller and asynchronous commands received from the second controller.

9. A method for sending a command to nodes of a robotic arm of a robotic surgical system, the method comprising:
performing the following in a robotic surgical system comprising a first controller, a second controller, and a plurality of robotic arms, each robotic arm comprising a plurality of nodes arranged in a ring network:
with the first controller, sending the second controller a single message comprising a plurality of individual multi-node messages, wherein each individual multi-node message is associated with a different robotic arm and comprises a plurality of packets, each packet associated with a different node, and
with the second controller, separating out each individual multi-node message from the single message and sending each robotic arm its associated individual multi-node message, wherein:
in communication cycle N−1, the second controller receives feedback from a command sent to a given robotic arm in a previous communication cycle;

in communication cycle N, the second controller generates a command based on the received feedback; and in communication cycle N+1, the second controller sends the generated command to the given robotic arm.

10. The method of claim 9, wherein the feedback is received at an end of communication cycle N−1, and wherein the generated command is sent to the given robotic arm at a beginning of communication cycle N+1.

11. The method of claim 9, wherein the command sent to the given robotic arm in the previous communication cycle comprises a synchronous command.

12. The method of claim 9, wherein communication cycles N−1, N, and N+1 are defined by a constant cycle time to support isochronous real-time data transfer.

13. The method of claim 9, wherein each node is configured to perform an on-the-fly message exchange for its associated packet in the multi-node message.

14. The method of claim 9, wherein the plurality of nodes include at least one node having one or more of the following components: a node controller, a single motor, a dual motor, a wireless tool interface, a force/torque sensor, and an input/output board.

15. The method of claim 9 further comprising in communication cycle N:

sending a command generated in communication cycle N−1 to the given robotic arm; and receiving feedback from the given robotic arm to a command sent to the given robotic arm in communication cycle N−1.

16. A robotic surgical system comprising:

a plurality of robotic arms, each robotic arm comprising a plurality of nodes arranged in a ring network;

a first controller; and a second controller configured to communicate synchronous and asynchronous information between the second controller and the plurality of nodes of a given robotic arm in a communication cycle;

wherein the first controller is configured to send the second controller a single message comprising a plurality of individual multi-node messages, wherein each individual multi-node message is associated with a different robotic arm and comprises a plurality of packets, each packet associated with a different node; and wherein the second controller is configured to separate out each individual multi-node message from the single message and send each robotic arm its associated individual multi-node message.

17. The robotic surgical system of claim 16, wherein the communication cycle is defined by a constant cycle time to support isochronous real-time data transfer.

18. The robotic surgical system of claim 16 further comprising means for pipelining a command generation and transmittal process across a plurality of communication cycles.

19. The robotic surgical system of claim 16:

wherein during one part of a communication cycle between the second controller and the plurality of nodes of a given robotic arm, the second controller is configured to send a synchronous command to each node of the given robotic arm using the multi-node message and each node of the given robotic arm is configured to send a response to an asynchronous command sent to that node in a previous communication cycle; and wherein during another part of the communication cycle between the second controller and the plurality of nodes of the given robotic arm, the second controller is configured to send an asynchronous command to each node of the given robotic arm using the multi-node message and each node of the given robotic arm is configured to send a response to a synchronous command received by that node in a previous communication cycle.

20. The robotic surgical system of claim 16, wherein:

in communication cycle N−1, the second controller receives feedback from a command sent to a given robotic arm in a previous communication cycle;

in communication cycle N, the second controller generates a command based on the received feedback; and in communication cycle N+1, the second controller sends the generated command to the given robotic arm.

* * * * *